(12) United States Patent
Nakayama et al.

(10) Patent No.: US 6,403,666 B1
(45) Date of Patent: Jun. 11, 2002

(54) POLYOLEFIN BASE POROUS FILM

(75) Inventors: Nobuhiko Nakayama, Hikari; Masaji Enokuchi, Tokuyama, both of (JP)

(73) Assignee: Tokuyama Corporation, Yamaguchi-ken (JP)

( * ) Notice: Subject to any disclaimer, the term of this patent is extended or adjusted under 35 U.S.C. 154(b) by 0 days.

(21) Appl. No.: 09/443,467

(22) Filed: Nov. 19, 1999

(30) Foreign Application Priority Data

Nov. 19, 1998 (JP) ............................................ 10-329583
Mar. 19, 1999 (JP) ............................................ 11-075149

(51) Int. Cl.$^7$ ................................................. C08F 10/02

(52) U.S. Cl. .......................... 521/142; 521/92; 521/97; 521/98; 264/45.3; 442/327

(58) Field of Search ........................ 521/142, 92, 97, 521/98; 264/45.3; 442/327

(56) References Cited

U.S. PATENT DOCUMENTS 3,362,924 A    1/1968    Eastman

FOREIGN PATENT DOCUMENTS

| EP | 0379913 | 8/1990 |
| JP | 53-28644 | 3/1978 |

OTHER PUBLICATIONS

Database WPI, Section Ch, Week 198420 Derwent Publications Ltd., London, GB; AN 1984–124653 XP002129876 & JP 59 062117 A (Mitsubishi Chem. Ind. Ltd.), Apr. 9, 1984.

Database WPI, Section Ch, Week 198841 Derwent Publications Ltd., London, GB; AN 1988–288746 XP002129877 & JP 63 210144 A (Toyuyama Soda KK), Aug. 31, 1988.

*Primary Examiner*—John M. Cooney, Jr.
(74) *Attorney, Agent, or Firm*—Wenderoth, Lind & Ponack, L.L.P.

(57) ABSTRACT

Provided is a polyolefin base porous film comprising a polyolefin composition in which calcium carbonate particles, preferably calcium carbonate particles subjected to surface treatment with chain carboxylic acid having 3 to 6 carbon atoms are dispersed. This polyolefin base porous film is characterized by that the leached solution with water has a pH which falls in the vicinity of neutrality and has a low stimulation to the skin, and therefore it is useful for goods contacting human bodies, particularly a back sheet for a sanitary napkin.

12 Claims, No Drawings

POLYOLEFIN BASE POROUS FILM

BACKGROUND OF THE INVENTION

1. Field of the Invention

The present invention relates to a polyolefin porous film and a production process for the same. More specifically, the present invention relates to a polyolefin porous film in which calcium carbonate particles are used as an inorganic filler for making the film porous and a production process for the same.

2. Description of the Prior Art

There has so far been known a method in which a film obtained by melting and molding a polyolefin composition in which an inorganic filler is dispersed is subjected to stretching treatment to cause interfacial peeling between the above inorganic filler and polyolefin to thereby produce a polyolefin porous film. The polyolefin porous film obtained by such method has good gas permeability and moisture permeability, but on the other hand, it has liquid nonpermeability, so that it is effectively used for back sheets for a sanitary napkin and a paper diaper, medical or sanitary materials such as a disposable type operation gown, and other various materials such as clothes for rainy weather and industrial materials.

It is known that various inorganic particles are used as the inorganic filler used for a production process for such polyolefin porous film. Among them, calcium carbonate particles have good dispersibility and are liable to cause interfacial peeling from polyolefin, so that the homogeneous porous structure can be formed. In addition, they are relatively inexpensive and therefore advantageously used.

However, calcium carbonate is such a strongly basic compound that the pH of the aqueous suspension exceeds 9. A porous film which is produced using such calcium carbonate particles as described above stimulates the skin in uses where it contacts human bodies in many cases, so that it has been limited in use in a certain case. In particular, a sanitary napkin is used while contacting directly the skin, and therefore it exerts a large influence and has had a problem in use for a back sheet. Accordingly, a porous film using particles of neutral compounds such as barium sulfate and the like has to be used for such uses, but the above barium sulfate particles are slightly inferior in properties such as dispersibility as compared with those of calcium carbonate particles and in addition thereto, they are expensive, so that they are only a little far from being satisfactory.

Described in Japanese Patent Application Laid-Open No. 28644/1978 is a polyolefin-stretched composition obtained by stretching a composition comprising an active filler obtained by covering the surface of an inorganic filler with a polymerizable organic monomer having an ethylenically double bond and polyolefin at a temperature which is lower by 5 to 30° C. than the melting point of the polyolefin. Further, given therein are acrylic acid as the example of the preceding polymerizable organic monomer having an ethylenically double bond and calcium carbonate and various compounds as the examples of the inorganic filler described above. However, an object of such techniques is to obtain molded articles having a small width such as monofilaments and tapes having an excellent mechanical strength, and it is not intended to produce a porous film. In addition thereto, the stretching temperature is set at such high temperature as described above for the purpose of obtaining the high strength. When a sheet-shaped article is stretched at such high temperature, it is difficult to cause interfacial peeling between an inorganic filler and polyolefin, so that a porous film having good properties can not be produced.

Under such circumstances as described above, it is desired in this industry to develop a polyolefin base porous film which is produced using calcium carbonate and has a low stimulation to skin.

Accordingly, an object of the present invention is to provide such polyolefin base porous film as described above.

SUMMARY OF THE INVENTION

Intensive researches continued by the present inventors have resulted in successfully developing a polyolefin base porous film which meets the object described above.

Thus, according to the present invention, provided is a polyolefin base porous film characterized by comprising a polyolefin composition in which calcium carbonate particles are dispersed and having a pH of a leached solution with water which falls in the vicinity of neutrality.

Such polyolefin base porous film is obtained by using calcium carbonate particles subjected to surface treatment with chain carboxylic acid having 3 to 6 carbon atoms as the calcium carbonate particles according to the preferred embodiment of the present invention. Hence, according to the present invention, provided is the preceding polyolefin base porous film produced by using the calcium carbonate particles as subjected to surface treatment in such manner as described above.

According to the present invention, further provided as well is a production process for the preceding polyolefin base porous film, comprising the steps of molding a polyolefin composition in which calcium carbonate particles subjected to surface treatment with chain carboxylic acid having 3 to 6 carbon atoms are dispersed into a sheet and then stretching it at least in a uniaxial direction.

DETAILED DESCRIPTION OF THE INVENTION

Though the polyolefin base porous film of the present invention is a polyolefin base porous film obtained by stretching a polyolefin composition in which calcium carbonate particles are dispersed to thereby make it porous, the pH of a leached solution with water falls in the vicinity of neutrality, wherein a pH of the leached solution with water is obtained by measuring a pH of a leached solution obtained by dipping 10 g of the polyolefin base porous film in 100 ml of water at a temperature of 25° C. for 5 minutes. The pH may be determined by any method. Usually, it is determined by a method in which 25 ml of a leached solution is sampled and three drops of a phenolphthalein reagent solution are added thereto to observe whether or not the solution presents a crimson color and in which another 25 ml of the leached solution is sampled and one drop of a Methyl Orange reagent solution is added thereto to observe whether or not the solution presents a red color.

In the present invention, the pH of the leached solution which falls in the vicinity of neutrality means a pH falling in a range where in the preceding measurement of pH, a crimson color is not presented by addition of a phenolphthalein reagent solution and in which a red color is not presented by addition of a Methyl Orange reagent solution reagent solution. This corresponds to a pH falling in a range of 4.4 to 8.3.

The method for determining a pH of a leached solution with water is based on an acid and alkali test described in a sanitary product disposal standard notified (on May 24, 1966) as the Welfare Ministry notification No. 285 in Japan.

The polyolefin base porous film of the present invention having such properties can be: obtained by using the calcium carbonate particles subjected to surface treatment with chain carboxylic acid having 3 to 6 carbon atoms. In this case, both of heavy calcium carbonate particles and heavy calcium carbonate particles can be used for the calcium carbonate particles subjected to the surface treatment described above without limitations. They have usually an average particle diameter of 0.1 to 50 μm, preferably 0.5 to 10 μm. If the calcium carbonate particles have an average particle diameter larger than 50 μm, the maximum pore diameter revealed on the film after stretching tends to grow larger to reduce a minuteness of the pore. On the other hand, if the average particle diameter is smaller than 0.1 μm, the molding property of the film becomes inferior due to the inferior dispersion or uneven stretching is caused, so that the homogeneous porous film tends to be unobtainable.

The chain carboxylic acid reacted onto the surface of the calcium carbonate particles described above has 3 to 6 carbon atoms. When the surface of the calcium carbonate particles is treated with such chain carboxylic fatty acid, carbon dioxide gas is produced on the above surface to bring about neutralization reaction, and the calcium salt of the chain carboxylic acid is formed. Accordingly, the surface of the calcium carbonate particles is covered with the resulting chain carboxylic acid calcium salt, and the basic property is notably weakened. The cause for which the basic property is thus weakened by allowing the surface of the calcium carbonate particles to be covered with the calcium salt of the chain carboxylic acid is uncertain, but it is estimated due to that when the calcium salt of the above chain carboxylic acid is immersed in water, it is dissociated more preferentially than calcium carbonate to inhibit calcium carbonate from being dissolved from the inside of the particles.

In addition thereto, the calcium carbonate particles subjected to such surface treatment holds satisfactorily an excellent, dispersibility and interfacial peeling property which are intrinsic to the calcium carbonate particles without being reduced so much. Accordingly, the porous film which has a good porous structure and in which a leached solution with water has a pH falling in the vicinity of neutrality as described above can be obtained by using the calcium carbonate particles subjected to the above surface treatment.

In the present invention; chain carboxylic acid may be not only linear but also may have branched chains or may be not only monocarboxylyc acid but also may have plural carboxyl groups. To be specific, it includes saturated monobasic acids such as propionic acid, butyric acid, valeric acid and caproic acid; saturated dibasic acids such as succinic acid and adipic acid; unsaturated monocarboxylic acids such as acrylic acid, methacrylic acid and pentenoic acid; and unsaturated dicarboxylic acids such as maleic acid.

In the present invention, in order to obtain the porous film which is closer to neutrality, unsaturated carboxylic acids having polymerizable unsaturated groups, such as acrylic acid, methacrylic acid and 4-pentenoic acid are preferably used as the chain carboxylic acid. In particular, acrylic acid and methacrylic acid are preferably used. It is estimated that when such carboxylic acids are used, the polymerization reaction of the above polymerizable unsaturated groups is slightly caused in the surface treatment and melting and mixing with polyolefin, and therefore the calcium salt of the chain carboxylic acid firmly covers reticulately the calcium carbonate particles in the form of polymers and that as a result thereof, the effect of neutralization is elevated.

In the present invention, in order to react the chain carboxylic acid onto the surface of the calcium carbonate particles, the chain carboxylic acid may usually be contacted with the surface of the calcium carbonate particles at a temperature of 0 to 100° C., preferably 20 to 80° C. When unsaturated carboxylic acids are used as the carboxylic acid, there is the risk that the polymerizable unsaturated groups are polymerized to an excess degree if the treating temperature is high to cause coagulation of the particles, so that the treating temperature is particularly preferably 30 to 60° C. Contacting of the chain carboxylic acid with the surface of the calcium carbonate particles in such manner as described above brings about neutralization reaction to produce carbon dioxide gas, and the calcium salt of the chain carboxylic acid is formed. A method for contacting shall not be restricted and includes a method in which chain carboxylic acid is sprayed while stirring calcium carbonate particles by means of a super mixer and a method in which chain carboxylic acid is mixed with the suspension of calcium carbonate particles and the mixture is stirred and dried.

In the surface treatment, the chain carboxylic acid is used in such an amount that 25 ml of a 10% aqueous suspension of the surface-treated calcium carbonate particles has a pH falling in a range where a crimson color is not presented by adding three drops of a phenolphthalein reagent solution and a red color is not presented by adding one drop of a Methyl Orange reagent solution, that is, a range of 4.4. to 8.3. The amount of the chain carboxylic acid fixed on the surface of the used calcium carbonate particles in the form of a salt is varied depending on the particle diameter of the calcium carbonate particles used and the kind of the chain carboxylic acid used, and it falls usually in, a range of 0.1 to 10 parts by weight, preferably 0.5 to 5 parts by weight per 100 parts by weight of the calcium carbonate particles. The surface treating time is varied depending on the kind of the chain carboxylic acid and the temperature condition, and it is usually 10 minutes to 12 hours, preferably 30 minutes to 5 hours.

The calcium carbonate particles subjected to surface treatment with the chain carboxylic acid described above are reduced in dispersibility to polyolefin in a certain case, and therefore in such case, higher fatty acids or salts thereof, surfactants and the like are preferably blended. In particular, higher fatty acids having 8 to 24 carbon atoms, preferably 10 to 14 carbon atoms or salts thereof are preferably blended. To be specific, examples thereof include capric acid, lauric acid, myristic acid, palmitic acid, stearic acid, arachidic acid, and salts thereof. Metal elements constituting these salts include elements of the 2nd group in the periodic table (e.g., Ca, Mg and the like), elements of the 12th group in the periodic table (e.g., Zn and the like), elements of the 12th group in the periodic table (e.g., Al and the like) and elements of the 14th group in the periodic table (e.g., Pb, Sn and the like). The blending amount of such higher fatty acid or a salt thereof is usually 0.1 to 10 parts by weight, more preferably 0.5 to 5 parts by weight per 100 parts by weight of the calcium carbonate particles.

In particular, in order to enhance the dispersibility, the surface-treated calcium carbonate particles subjected to surface treatment with the preceding chain carboxylic acid having 3 to 6 carbon atoms are preferably subjected to secondary surface treatment with the higher fatty acid or salt thereof described above to cover the surface of the above particles with the higher fatty acid or salt thereof. The secondary surface treat with the higher fatty acid or salt thereof described above may be carried out by the same method as that of the surface treatment with the preceding chain carboxylic acid having 3 to 6 carbon atoms. When the higher fatty acid or salt thereof is a solid matter, it may be contacted with the calcium carbonate particles by dry-blending by means of a mixer such as a super mixer and a Henschel mixer, or a solution prepared by dissolving the higher fatty acid or salt thereof in an organic solvent such as hexane, heptane, octane, methanol, ethanol, toluene and xylene may be sprayed on ;the calcium carbonate particles and then dried.

The treating temperature in the secondary surface treatment is usually 0 to 100° C., preferably 20 to 80° C. When the calcium carbonate particles subjected to the surface treatment with unsaturated carboxylic acid as the chain carboxylic acid are subjected to the secondary surface treatment, there is the risk that if the treating temperature is high, the polymerizable unsaturated groups are polymerized between the particles to cause coagulation of the particles, and therefore the above treating temperature is particularly preferably 30 to 60° C.

In order to carry out the even surface treatment at a good operability at the treating temperature described above, higher fatty acids such as lauric acid and stearic acid which are liquid are preferably used to carry out the treatment at the above treating temperature by spraying. These higher fatty acids tend to be a little inferior in an improving effect of the dispersibility as compared with those of the salts thereof. If the desired dispersibility is not obtained even by using the higher fatty acids, the salts of the above higher fatty acids are preferably used in an amount falling in a range of the treating amount described above to further cover the surface of the preceding calcium carbonate subjected to the secondary surface treatment by dry blending, or the salts of the higher fatty acids are preferably blended with polyolefin separately from the calcium carbonate particles. The salt of the higher fatty acid which gives a particularly high dispersibility-improving effect to the calcium carbonate particles subjected to the surface treatment with the chain carboxylic acid is the zinc salt.

In the present invention, polyolefin includes α-olefin homopolymers (e.g., polyethylene, polypropylene, polybutene-1 and poly-4-methyl-1-pentene), copolymers of two or more kinds of α-olefins, copolymers of α-olefins with other monomers copolymerizable therewith, and mixtures thereof. Preferred are polyethylenes such as high density polyethylene, low density polyethylene and linear low density polyethylene. The other monomers copolymerizable with α-olefins shall not specifically be restricted, and publicly known ones can be used. In general, however, α-olefins having 2 to 8 carbon atoms are suitable. In the present invention, the polyolefins which can preferably be used are copolymers of ethylene with α-olefins. To be specific, preferred are copolymers of ethylene with α-olefins having 4 to 8 carbon atoms such as butene-1, hexene-1, 4-methyl-1-penetene and octene-1. In particular, linear low density polyethylene having a density of 0.910 to 0.930 is preferred.

In the present invention, the blending proportion of the calcium carbonate particles subjected to the surface treatment with the chain carboxylic acid to the polyolefin is 20 to 70% by weight, preferably 30 to 60% by weight of the polyolefin and 30 to 80% by weight, preferably 40 to 70% by weight of the calcium carbonate particles. If the blending amount of the calcium carbonate particles is smaller than 30% by weight, there is the risk that the porosity is not sufficiently brought about in stretching the film. On the other hand, if it is larger than 80% by weight, there is the risk that inferior molding is caused when molded into a sheet and the stretchability is reduced.

The polyolefin base porous film of the present invention can be obtained by molding the polyolefin composition in which the calcium carbonate particles subjected to surface treatment with the chain carboxylic acid into a sheet and then stretching it at least in a uniaxial direction. When the above calcium carbonate particles subjected to the surface treatment contain coarse coagulated particles produced in the surface treatment described above, they are preferably classified to remove these coarse coagulated particles and then used.

A method for mixing polyolefin with the surface-treated calcium carbonate particles to obtain the polyolefin composition in which the above particles are dispersed shall not specifically be restricted, and publicly known methods can be employed. Examples thereof include a method in which the components are mixed by means of a super mixer or a Henschel mixer and then pelletized by means of a high kneading type two-shaft extruding machine. Further, in the mixing described above, additives such as antioxidants, weather resistant agents, pigments, plasticizers and antistatic agents and in addition thereto, additives such as silicon oils and waxes for obtaining the even stretchability may be blended according to conventional methods.

A method for molding the polyolefin composition thus obtained into a sheet-shaped article shall not specifically be restricted as well, and an inflation molding method and a T-die molding method are generally used.

The film can be made porous by stretching the sheet-shaped article described above. Conventional stretching methods can be employed for the stretching method. In general, single-shaft stretching by rolls, single-shaft stretching followed by sequential two-shaft molding by means of a tenter stretching machine or simultaneous two-shaft molding is employed, and two-shaft molding is particularly preferred from the viewpoint of balance in the strength of the film.

In order to obtain the good porosity, the stretching is carried out preferably at a stretching temperature falling between 20° C. and a temperature which is lower by 35° C. than the melting point of the polyolefin. The particularly preferred stretching temperature is a temperature falling between 30° C. and a temperature which is lower by 40° C. than the melting point of the polyolefin. In the present invention, the melting point of the polyolefin is shown as a temperature at the top position of a maximum peak measured by means of a differential scanning type calorimeter. When the stretching temperature is lower than 20° C., the stretching load goes up, and the even stretching becomes impossible. On the other hand, when the stretching temperature exceeds a temperature which is lower by 35° C. than the melting point of the polyolefin, interfacial peeling between the surface-treated calcium carbonate particles and the polyolefin is hard to be caused, and the porous film having good properties comes to be unobtainable.

In order to make the broad sheet-shaped article porous at the stretching temperature described above without breaking, the stretching magnification is usually 1.1 to 5 times, more preferably 1.3 to 3.5 times in terms of an area magnification. When the area magnification is smaller than 1.4 time, the film can not evenly be stretched, which makes it difficult to make the film porous. On the other hand, when the area magnification is larger than 5 times, breakage of the film is liable to be caused, and the film tends to be reduced in a strength. Usually, the film is stretched by 1.1 to 3.5 times in a uniaxial direction. In the case of biaxial stretching, the film is preferably further stretched in a direction orthogonal to the above uniaxial direction in a range which does not exceed the area magnification described above.

Such stretching allows voids to be produced in the circumference of the calcium carbonate particles dispersed in the film, and the resin becomes micro fibril-shaped, whereby a network structure is formed in the film by a lot of continuously communicated pores.

The polyolefin base porous film of the present invention obtained by the methods described above has a thickness of 10 to 100 $\mu$m, preferably 15 to 50 $\mu$m. It has a void ratio of 10 to 60%, preferably 15 to 40%, and the continuously communicated pores have a maximum pore diameter of 10 $\mu$m or less, preferably 5 $\mu$m or less and particularly preferably 2 $\mu$m or less. When the above porous film is used as a medical or sanitary material such as a back sheet for a sanitary napkin, it has to have a water vapor transmission rate of 500 $\mu$m$^2$·24 hr or more, preferably 1000 to 6000 g/m$^2$·24 hr and particularly preferably 1500 to 5500 g/m$^2$·24 hr, a gas permeability of 5000 seconds/100 ml or less, preferably 100 to 4000 seconds/100 ml and particularly preferably 300 to 3500 seconds/100 ml and a water resistant pressure of 200 kPa or more, preferably 10 kPa or more.

Though the calcium carbonate particles are used as a filler for the polyolefin base porous film of the present invention, the leached solution thereof has a pH falling in the vicinity of neutrality as described above, and therefore the skin is not stimulated even if it is used for uses where it contacts human bodies in many cases. Further, it can be produced at a lower cost since the calcium carbonate particles are used. The film, produced using the calcium carbonate particles subjected to surface treatment with chain carboxylic acid having 3 to 6 carbon atoms is made well porous and has a high moisture permeability and a high liquid non-permeability.

Accordingly, the polyolefin base porous film of the present invention having such properties can effectively be used for various materials such as medical materials, sanitary materials, clothes for rainy weather, other goods having the possibility to contact human bodies, and industrial materials. In particular, it can preferably be used as a back sheet for a sanitary napkin.

EXAMPLES

The present invention shall specifically be explained with reference to examples, but the present invention shall by no means be restricted by these examples.

The physical properties of the polyolefin base porous film of the present invention were measured by the following methods:
(1) Thickness: determined by means of dial gauge based on JIS K-6734.
(2) Void ratio: hole volume of the porous film was determined by a mercury porosimeter method.
(3) Maximum pore diameter: determined by an ethanol bubble point method
(4) Gas permeability: determined according to JIS P8117 (Gurley gas permeability).
(5) Water vapor transmission rate: determined on the conditions of a temperature of 40° C. and a relative humidity of 90% based on a JIS Z0208 method.
(6) Water resistant pressure: determined based on a JIS L1092B method.
(7) pH of a leached solution: 25 ml of a sample was taken from a leached solution obtained by dipping 10 g of the polyolefin base porous film in 100 ml of water at a temperature of 20° C. for 5 minutes, and three drops of a phenolphthalein reagent solution were added thereto to observe whether or not the solution presented a crimson color, wherein when the crimson color was presented (alkaline), it was recorded with ×, and when the crimson color was not presented, it was recorded with ○. Then, another 25 ml of the leached solution was sampled, and one drop of a Methyl Orange reagent solution was added thereto to observe whether or not the solution presented a red color, wherein when the red color was presented (acid), it was recorded with ×, and when the red color was not presented, it was recorded with ○. Further, the actual pH of the leached solution described above was measured by means of a pH meter.
(8) Evaluation of appearance: the polyolefin base porous film was observed by five magnifications by means of a universal projector (PROFILE PROJECTOR V-12) manufactured by Nikon Co., Ltd. while applying light from under the film to count ten times the number of the coarse coagulated matters (particle diameter: 50 $\mu$m or more) of the calcium carbonate particles and, and it was evaluated by converting the average value thereof to a value per 1 m$^2$.

Production Example 1

Hundred parts by heavy calcium carbonate particles having an average particle diameter of 1.2 $\mu$m was put into a super mixer and stirred at 40° C. for one hour while spraying little by little 2.0 parts by weight of acrylic acid from a small nozzle. During this operation for subjecting the heavy calcium carbonate particles to surface treatment, carbon dioxide, gas was observed to be produced on the surface of the heavy calcium carbonate particles by neutralization of acrylic acid.

The surface composition of the surface-treated calcium carbonate particles thus obtained was determined by a diffuse reflection method by means of a Fourier transform infrared spectroscope. Further, the surface composition of the feed calcium carbonate particles was determined for the sake of comparison in the same manner. A difference in a spectrum between both was consistent with a spectrum obtained from calcium acrylate, and it could be confirmed from this that the surface composition of the surface-treated calcium carbonate particles was covered with calcium acrylate. Further, the surface-treated calcium carbonate particles and the feed calcium carbonate particles were subjected to thermogravimetric measurement. As a result thereof, it could be confirmed that while a change in the weight from a room temperature up to 500° C. was not substantially observed in the feed calcium carbonate particles, the weight was reduced by 1.4% in the surface-treated calcium carbonate particles. A weight change curve in this case showed the same tendency as in a weight change curve in the same measurement of calcium acrylate. It could be confirmed from this weight variation that the reaction percentage of acrylic acid onto the surface of the calcium carbonate particles was about 70%.

A 10% aqueous suspension of the surface-treated calcium carbonate particles thus obtained had a pH of 7.2.

Production Example 2

Hundred parts by weight of heavy calcium carbonate particles was subjected to surface treatment with 2.0 parts by weight of acrylic acid in the same manner as in Production Example 1, and then the resulting calcium carbonate particles were further subjected to surface treatment with one part by weight of lauric acid. A 10% aqueous suspension of the surface-treated calcium carbonate particles thus obtained had a pH of 7.2.

Production Example 3

The same treatment as in Production Example 2 was repeated, except that in Production Example 2, one part by weight of stearic acid was substituted for one part by weight of lauric acid to carry out the surface treatment. A 10% aqueous suspension of the surface-treated calcium carbonate particles thus obtained had a pH of 7.2.

Production Example 4

Hundred parts by weight of the heavy calcium carbonate particles subjected to surface treatment with acrylic acid and lauric acid which were obtained according to Production Example 2 was sampled, and this was dry-blended with one part by weight of zinc stearate, whereby they were further subjected to surface treatment. A 10% aqueous suspension of the surface-treated calcium carbonate particles thus obtained had a pH of 7.2.

Production Example 5

Heavy calcium carbonate particles subjected to surface treatment with n-varelic acid were obtained in the same manner as in Production Example 1, except that in Production Example 1, the heavy calcium carbonate particles having an average particle diameter of 1.0 µm were used and n-varelic acid was substituted for acrylic acid. During the operation, carbon dioxide gas was observed to be produced on the surface of the heavy calcium carbonate particles by a neutralization reaction of n-varelic acid.

It was confirmed by the same confirming method as in Production Example 1 that the surface of the surface-treated calcium carbonate particles thus obtained was covered with calcium n-varelate. Further, they were subjected to thermogravimetric measurement to find that a change in the weight from a room temperature up to 500° C. was 1.5%, and it could be confirmed from this that about 75% in terms of n-varelic acid was reacted onto the surface.

After finishing the operation described above, one part by weight of stearic acid was used to further carry out surface treatment.

A 10% aqueous suspension of the surface-treated calcium carbonate particles thus obtained had a pH of 7.9.

Production Example 6

Heavy calcium carbonate particles subjected to surface treatment with methacrylic acid were obtained in the same manner as in Production Example 1, except that in Production Example 1, the heavy calcium carbonate particles having an average particle diameter of 1.0 µm were used and methacrylic acid was substituted for acrylic acid. During the operation, carbon dioxide gas was observed to be produced on the surface of the heavy calcium carbonate particles by a neutralization reaction of methacrylic acid.

It was confirmed by the same confirming method as in Production Example 1 that the surface of the surface-treated calcium carbonate particles thus obtained was covered with calcium methacrylate. Further, they were subjected to thermogravimetric measurement to find that a change in the weight from a room temperature up to 500° C. was 1.6%, and it could be confirmed from this that about 80% in terms of methacrylic acid was reacted onto the surface.

After finishing the operation described above, one part by weight of stearic acid was used to further carry out surface treatment.

A 10% aqueous suspension of the surface-treated calcium carbonate particles thus obtained had a pH of 8.2.

Production Example 7

The same procedure as in Production Example 3 was repeated, except that in Production Example 3, the treated amount of acrylic acid onto the surface of the heavy calcium carbonate particles was changed to 1.0 part by weight. After treated with acrylic acid, the surface-treated calcium carbonate particles were subjected to thermogravimetric measurement to find that a change in the weight from a room temperature up to 500° C. was 0.7%, and it could be confirmed from this that about 70% in terms of acrylic acid was reacted onto the surface.

A 10% aqueous suspension of the surface-treated calcium carbonate particles thus obtained had a pH of 7.7.

Production Example 8

The same procedure as in Production Example 3 was repeated, except that in Production Example 3, the treated amount of acrylic acid onto the surface of the heavy calcium carbonate particles was changed to 4.0 parts by weight. After treated with acrylic acid, the surface-treated calcium carbonate particles were subjected to thermogravimetric measurement to find that a change in the weight from a room temperature up to 500° C. was 2.0%, and it could be confirmed from this that about 50% in terms of acrylic acid was reacted onto the surface.

A 10% aqueous suspension of the surface-treated calcium carbonate particles thus obtained had a pH of 6.8.

Comparative Production Example 1

Heavy calcium carbonate particles subjected to surface treatment with lauric acid were obtained in the same manner as in Production Example 1, except that in Production Example 1, lauric acid was substituted for acrylic acid. After finishing the operation described above, they were further subjected to surface treatment with one part by weight of stearic acid. A 10% aqueous suspension of the surface-treated calcium carbonate particles thus obtained had a pH of 8.9.

Example 1

A composition comprising 50% by weight of linear low density polyethylene (brand name: Idemitsu PE0234CL, melting point: 125° C.), 50% by weight of the surface-treated calcium carbonate particles obtained in Production Example 1 and a small amount of a stabilizer was mixed by means: of a super mixer and then molten, kneaded and extruded by means of a two-shaft extruding machine having a diameter of 50 mm to thereby obtain pellets. Then, a sheet-shaped article having a thickness of 40 µm was molded from these pellets by means of a 40 mm T-die extruding machine and stretched at a stretching temperature of 70° C. by 1.5 magnification in a longitudinal (MD) direction and by 1.3 magnification in a lateral (TD) direction, whereby a porous film having a thickness of 30 µm was obtained. The properties of the porous film thus obtained are shown in Table 1.

Further, a sanitary napkin in which the porous film described above was used for a back sheet was produced.

Example 2

A porous film was obtained in the same manner as in Example 1, except that in Example 1, the surface-treated calcium carbonate particles obtained in Production Example 2 were used. The properties of the porous film thus obtained are shown in Table 1.

Further, a paper diaper in which the porous film described above was used for a back sheet was produced.

Example 3

A porous film was obtained in the same manner as in Example 1, except that in Example 1, the surface-treated calcium carbonate particles obtained in Production Example 3 were used. The properties of the porous film thus obtained are shown in Table 1.

Further, a sanitary napkin in which the porous film described above was used for a back sheet was produced.

Example 4

A porous film was obtained in the same manner as in Example 1, except in Example 1, that the surface-treated calcium carbonate particles obtained in Production Example 4 were used. The properties of the porous film thus obtained are shown in Table 1.

Further, a sanitary napkin in which the porous film described above was used for a back sheet was produced.

Example 5

A porous film was obtained in the same manner as in Example 1, except that in Example 1, the surface-treated calcium carbonate particles obtained in Production Example 5 were used. The properties of the porous film thus obtained are shown in Table 1.

Further, a sanitary napkin in which the porous film described above was used for a back sheet was produced.

Example 6

A porous film was obtained in the same manner as in Example 1, except that in Example 1, the surface-treated calcium carbonate particles obtained in Production Example 6 were used. The properties of the porous film: thus obtained are shown in Table 1.

Further, a paper diaper in which the porous film described above was used for a back sheet was produced.

Example 7

A porous film was obtained in the same manner as in Example 1, except that in Example 1, the surface-treated calcium carbonate particles obtained in Production Example 7 were used. The properties of the porous film thus obtained are shown in Table 1.

Further, a sanitary napkin in which the porous film described above was used for a back sheet was produced.

Example 8

A porous film was obtained in the same manner as in Example 1, except that in Example, 1, the surface-treated calcium carbonate particles obtained in Production Example 8 were used. The properties of the porous film thus obtained are shown in Table 1.

Further, a sanitary napkin in which the porous film described above was used for a back sheet was produced.

Examples 9 and 10

Porous films were obtained in the same manner as in Example 3, except that in Example 3, the blending proportion of linear low density polyethylene to the surface-treated calcium carbonate particles was changed to 60/40 (Example 9) or 70/30 (Example 10) as shown in Table 1. The properties of the porous films thus obtained are shown in Table 1.

Further, sanitary napkins in which the respective porous films were used for a back sheet were produced respectively.

Example 11

A porous film having a thickness of 30 $\mu$m was obtained in the same manner as in Example 3, except that in Example 3, the sheet-shaped article having a thickness of 50 $\mu$m molded by extrusion was stretched by 2.0 magnifications in a longitudinal (MD) direction and by 1.5 magnification in a lateral (TD) direction. The properties of the porous film thus obtained are shown in Table 1.

Further, a paper diaper in which the porous film described above was used for a back sheet was produced.

Example 12

A porous film was obtained in the same manner as in Example 3, except that in Example 3, the stretching temperature was changed to 88° C. The properties of the porous film thus obtained are shown in Table 1.

Further, a sanitary napkin in which the porous film described above was used for a back sheet was produced.

Comparative Example 1

A porous film was obtained in the same manner as in Example 1, except that in Example 1, calcium carbonate particles which were not subjected to surface treatment with acrylic acid were substituted for the surface-treated calcium carbonate particles obtained in Production Example 1. The properties of the porous film thus obtained are shown in Table 1.

Comparative Example 2

A porous film was obtained in the same manner as in Example 1, except that in Example 1, the surface-treated calcium carbonate particles obtained in:Comparative Production Example 1 were substituted for the surface-treated calcium carbonate particles obtained in Production Example 1. The properties of the porous film thus obtained are shown in Table 1.

Comparative Example 3

A porous film was obtained in the same manner as in Example 3, except that in Example 3, the stretching temperature was changed to 100° C. The properties of the porous film thus obtained are shown in Table 1.

TABLE 1

| | Polyolefin/calcium carbonate (weight %) | Stretching magnification MD/TD | Properties of film | | | |
|---|---|---|---|---|---|---|
| | | | Thickness ($\mu$m) | Void ratio (%) | Gas permeability (sec./100 CC) | Water vapor transmission rate (g/m$^2$ · 24 HR) |
| Example 1 | 50/50 | 1.5/1.3 | 30 | 14 | 1900 | 3200 |
| Example 2 | 50/50 | 1.5/1.3 | 30 | 17 | 1500 | 3600 |
| Example 3 | 50/50 | 1.5/1.3 | 30 | 15 | 1500 | 3400 |
| Example 4 | 50/50 | 1.5/1.3 | 30 | 20 | 1400 | 4200 |

TABLE 1-continued

| | | | | | | |
|---|---|---|---|---|---|---|
| Example 5 | 50/50 | 1.5/1.3 | 30 | 16 | 1200 | 3600 |
| Example 6 | 50/50 | 1.5/1.3 | 30 | 16 | 1600 | 3600 |
| Example 7 | 50/50 | 1.5/1.3 | 30 | 15 | 1600 | 3200 |
| Example 8 | 50/50 | 1.5/1.3 | 30 | 15 | 1400 | 3500 |
| Example 9 | 60/40 | 1.5/1.3 | 30 | 12 | 3500 | 2000 |
| Example 10 | 30/70 | 1.5/1.3 | 30 | 34 | 350 | 5100 |
| Example 11 | 50/50 | 2.0/1.5 | 30 | 27 | 700 | 4300 |
| Example 12 | 50/50 | 1.5/1.3 | 30 | 11 | 3700 | 1200 |
| Comparative Example 1 | 50/50 | 1.5/1.3 | 30 | 17 | 1800 | 3200 |
| Comparative Example 2 | 50/50 | 1.5/1.3 | 30 | 17 | 1500 | 3500 |
| Comparative Example 3 | 50/50 | 1.5/1.3 | 30 | 4 | 7000 | 300 |

| | Properties of film | | | | | |
|---|---|---|---|---|---|---|
| | Maximum pore diameter ($\mu$m) | Water resistant pressure (kPa) | pH of leached solution | Phenol- phthalein | Methyl Orange | Coagulated matters (particles/m$^2$) |
| Example 1 | 1.8 | >200 | 7.2 | ○ | ○ | 800 |
| Example 2 | 1.0 | >200 | 7.2 | ○ | ○ | 600 |
| Example 3 | 1.1 | >200 | 7.0 | ○ | ○ | 550 |
| Example 4 | 0.6 | >200 | 7.2 | ○ | ○ | 100 |
| Example 5 | 1.5 | >200 | 7.9 | ○ | ○ | 650 |
| Example 6 | 1.1 | >200 | 7.7 | ○ | ○ | 550 |
| Example 7 | 1.3 | >200 | 7.7 | ○ | ○ | 550 |
| Example 8 | 1.0 | >200 | 6.8 | ○ | ○ | 600 |
| Example 9 | 0.8 | >200 | 6.9 | ○ | ○ | 450 |
| Example 10 | 1.8 | 120 | 7.2 | ○ | ○ | 650 |
| Example 11 | 2.2 | 70 | 7.1 | ○ | ○ | 550 |
| Example 12 | 1.4 | >200 | 7.0 | ○ | ○ | 500 |
| Comparative Example 1 | 1.6 | >200 | 9.2 | X (Crimson) | ○ | 700 |
| Comparative Example 2 | 1.0 | >200 | 8.8 | X (Crimson) | ○ | 500 |
| Comparative Example 3 | 1.2 | >200 | 6.2 | ○ | ○ | 100 |

What is claimed is:

1. A polyolefin base porous film characterized by comprising a polyolefin composition in which calcium carbonate particles are dispersed, wherein the calcium carbonate particles have been subjected to surface treatment with straight or branched chain carboxylic acid having 3 to 6 carbon atoms, and said film has a property such that a pH of water leached through the film falls in the vicinity of neutrality.

2. The polyolefin base porous film as described in claim 1, wherein the straight or branched chain carboxylic acid having 3 to 6 carbon atoms is unsaturated carboxylic acid.

3. The polyolefin base porous film as described in claim 1, wherein the polyolefin is polyethylene.

4. The polyolefin base porous film as described in claim 1, wherein the blending proportion of the polyolefin to the calcium carbonate particles is 20 to 70% by weight of the polyolefin and 80 to 30% by weight of the calcium carbonate particles.

5. The polyolefin base porous film as described in claim 1, further comprising a higher saturated fatty acid having 8 to 24 carbon atoms or a salt thereof in an amount of 0.1 to 10 parts by weight per 100 parts by weight of the calcium carbonate particles.

6. The polyolefin base porous film as described in claim 1, having a void ratio of 10 to 60%; continuously communicated pores which have a maximum pore diameter of 5 $\mu$m or less; a water vapor transmission rate of 1000 to 6000 g/m$^2$·24 hr; and a gas permeability of 100 to 4000 seconds/100 ml.

7. A production process for the polyolefin base porous film as described in claim 1, comprising the steps of molding a polyolefin composition in which calcium carbonate particles subjected to surface treatment with chain carboxylic acid having 3 to 6 carbon atoms are dispersed into a sheet and then Stretching it at least in a uniaxial direction.

8. The production process for the polyolefin base porous film as described in claim 7, wherein the polyolefin composition is blended with higher saturated fatty acid having 8 to 24 carbon atoms or a salt thereof of 0.1 to 10 parts by weight per 100 parts by weight of the calcium carbonate particles.

9. The production process for the polyolefin base porous film as described in claim 8, wherein the polyolefin composition is obtained by mixing polyolefin with calcium carbonate particles subjected to surface treatment with chain carboxylic acid having 3 to 6 carbon atoms and then further subjected to secondary surface treatment with higher saturated fatty acid having 8 to 24 carbon atoms or a salt thereof.

10. The production process for the polyolefin base porous film as described in claim 7, wherein the stretching is carried out at a temperature falling between 20° C. and a temperature which is lower by 35° C. than the melting point of the polyolefin.

11. An article of manufacture for contacting a human body, comprising the polyolefin base porous film as described in claim 1.

12. A sanitary napkin comprising the polyolefin base porous film as described in claim 1 which is used for a back sheet.

* * * * *